United States Patent [19]
Hellings et al.

[11] Patent Number: 5,975,079
[45] Date of Patent: *Nov. 2, 1999

[54] ANESTHESIA AND RESPIRATORY FACE MASK

[76] Inventors: Deborah Hellings; Brence Sell, both of P.O. Box 37247, Tallahassee, Fla. 32315

[ * ] Notice: This patent is subject to a terminal disclaimer.

[21] Appl. No.: 08/279,562

[22] Filed: Jul. 25, 1994

[51] Int. Cl.⁶ .................................................. A62B 18/08
[52] U.S. Cl. .............................. 128/206.24; 128/206.21; 128/206.26; 128/206.27; 128/206.28; 128/207.11
[58] Field of Search ........................ 128/203.29, 205.25, 128/206.21, 206.24, 206.26, 206.27, 206.28, 207.11, 208.23, 202.23

[56] References Cited

U.S. PATENT DOCUMENTS

| | | | |
|---|---|---|---|
| D. 293,613 | 1/1988 | Wingler | D29/7 |
| 2,625,155 | 1/1953 | Engelcles | 128/206.24 |
| 2,765,788 | 10/1956 | Raiche | 128/206.28 |
| 3,556,097 | 1/1971 | Wallace | 128/188 |
| 3,796,216 | 3/1974 | Schwarz | 128/145.7 |
| 3,815,596 | 6/1974 | Keener et al. | 128/188 |
| 3,946,742 | 3/1976 | Eross | 128/351 |
| 4,196,727 | 4/1980 | Veshaart et al. | 128/202.23 |
| 4,312,339 | 1/1982 | Thompson, Sr. | 128/205.25 |
| 4,337,767 | 7/1982 | Yahata | 128/206.28 |
| 4,582,054 | 4/1986 | Ferrer | 128/200.23 |
| 4,794,921 | 1/1989 | Lindkrist | 128/203.29 |
| 4,799,477 | 1/1989 | Lewis | 128/206.24 |
| 4,848,331 | 7/1989 | Northway-Meyer | 128/200.26 |
| 4,915,105 | 4/1990 | Lee | 128/207.18 |
| 4,944,310 | 7/1990 | Sullivan | 128/207.18 |
| 5,003,633 | 4/1991 | Itoh | 128/206.24 |
| 5,193,534 | 3/1993 | Peppler | 128/207.18 |

FOREIGN PATENT DOCUMENTS

| | | | |
|---|---|---|---|
| 1104122 | 4/1961 | Germany | 128/207.11 |

OTHER PUBLICATIONS

"Masks", Bay Medical, St. Petersburg, Florida, pp. 73, 74, & 81. Fall/1986.

Primary Examiner—John G. Weiss
Assistant Examiner—V. Srivastava
Attorney, Agent, or Firm—Carnes Cona & Dixon

[57] ABSTRACT

A disposable anesthesia mask is provided which has a top portion having an aperture, an encompassed side portion and an open bottom portion. Located on the open bottom portion is an inflatable sealing means, which provides a pneumatic seal between the mask and the patients face. The disposable mask is transparent and is located around the nasal bridge. This shape alleviates orbital pressure. Elongated hooks that are attached to the mask by a head strap plate provides the option of affixing a strap to the mask.

5 Claims, 4 Drawing Sheets

ANESTHESIA AND RESPIRATORY FACE MASK

BACKGROUND OF THE INVENTION

1. Field of the Invention

This invention relates to an anesthesia mask and more particularly to a disposable and visually transparent anesthesia mask.

2. Brief Description of the Prior Art

During surgery a patient is usually placed under anesthesia. The most common delivery system is composed of a canister containing the anesthesia gases, a system of regulating gas flow and patient breathing, and an anesthesia mask for delivery of the gas to the patient.

Several problems have been identified in the construction of anesthesia masks. Respiratory infection caused by cross-contamination from the use of reusable masks is a serious problem. Even though the masks are sterilized, this type of problem persists. In order to combat this problem, disposable masks have been proposed such as U.S. Pat. No. 3,815,596 issued to Keener et al.

Another problem encountered with anesthesia masks is gas leakage, which some have determined has an adverse medical effect on medical personnel who work with anesthesia. See for example U.S. Pat. No. 4,312,339, issued to Thompson, Sr. To solve this problem some, such as Thompson, Sr., have proposed masks that have scavenging circuits to recapture escaped gas. Although effective in protecting medical personnel, such devices are complex and costly.

Others have proposed using a cushioned surface to make contact with the patients face. Toward this end, two types of cushioning have been proposed. One type is illustrated in U.S. Pat. No. 3,556,097 issued to Wallace. The cushion consists of a foamed plastic material that contours to the patients face. A second type of cushion is an inflatable type of cushion as appears to be illustrated in Pat. No. Des. 293,613 issued to Wingler. The cushion is filled with air permitting a precise fit onto the patient's face, thereby providing a pneumatic seal.

A further problem of anesthesia mask construction, is the need for the anesthesia personnel to view the patents face so that any airway obstruction problems can be immediately identified. U.S. Pat. No. 4,848,331 issued to Northway-Meyer, disclosing a see-through mask has been disclosed in order to solve this problem.

Many anesthesia personnel require the use of both hands during surgery for purposes other than holding the mask to the patents face. Therefore, straps to hold the mask in place as found in the Keener patent, have been proposed. However, the use of these straps, as currently proposed make contact with the patient's face and are a source of discomfort for the patient before, during and after surgery.

A final problem associated with anesthesia masks that does not appear to be addressed by the current art is the ocular pressure enforced by the mask during use. This ocular pressure can be a source of exquisite discomfort and irritation and, in extreme cases, the pressure can cause an adverse medical condition in the patient.

The present invention, unlike the prior art, addresses each and every major concern associated with anesthesia masks. The present invention is disposable so that cross-contamination does not occur. The mask provides an inflatable sealing cushion so that a pneumatic seal is achieved without patient discomfort. Medical personnels exposure to anesthesia is eliminated. The mask is made of clear material so that medical personnel are in constant visual contact with a patients airway. The mask provides for strap attachment so that medical personnel gain the use of both hands during surgery. The present mask is constructed so that the straps used to attach the mask never communicate with the patient's face so that there is no strap discomfort. Finally, the mask is constructed so that it curves and contours around the mouth and nasal bridge for alleviating orbital irritation and deleting ocular pressure.

SUMMARY OF THE INVENTION

This invention provides for an apparatus which includes a disposable and visually transparent anesthesia mask. The mask is connected to the anesthesia breathing circuit which is connected to the anesthesia machine.

The disposable anesthesia mask and the breathing circuit are discarded after one use, hence eliminating bacteria traveling from one patient to another. The mask is constructed out of an inexpensive synthetic polymeric resin. This material is also clear and allows the anesthesia personnel visualization of the patient's airway.

The disposable anesthesia mask curves around the nasal bridge and provides a comfortable fit to the patient during induction and maintenance of the anesthesia. This shape also has an additional benefit of offering an easy and comfortable means of handling the mask by the anesthesia operator.

This mask is also equipped with a soft pliable seal that will conform to the patients facial features and maintain a hermetic seal. Further, optional straps are provided on the mask so that the straps will not communicate with the patient's face.

It is the object of the present invention to provide for an inexpensive anesthesia mask that is disposable and transparent.

It is another object of the present invention to provide for an anesthesia mask which confines the nose and mouth of a patient in order to eliminate orbital pressure.

It is another object of the present invention to provide for straps which attach to the anesthesia mask and does not contact the patient's facial skin.

DESCRIPTION OF THE PREFERRED EMBODIMENTS

Figure 1:
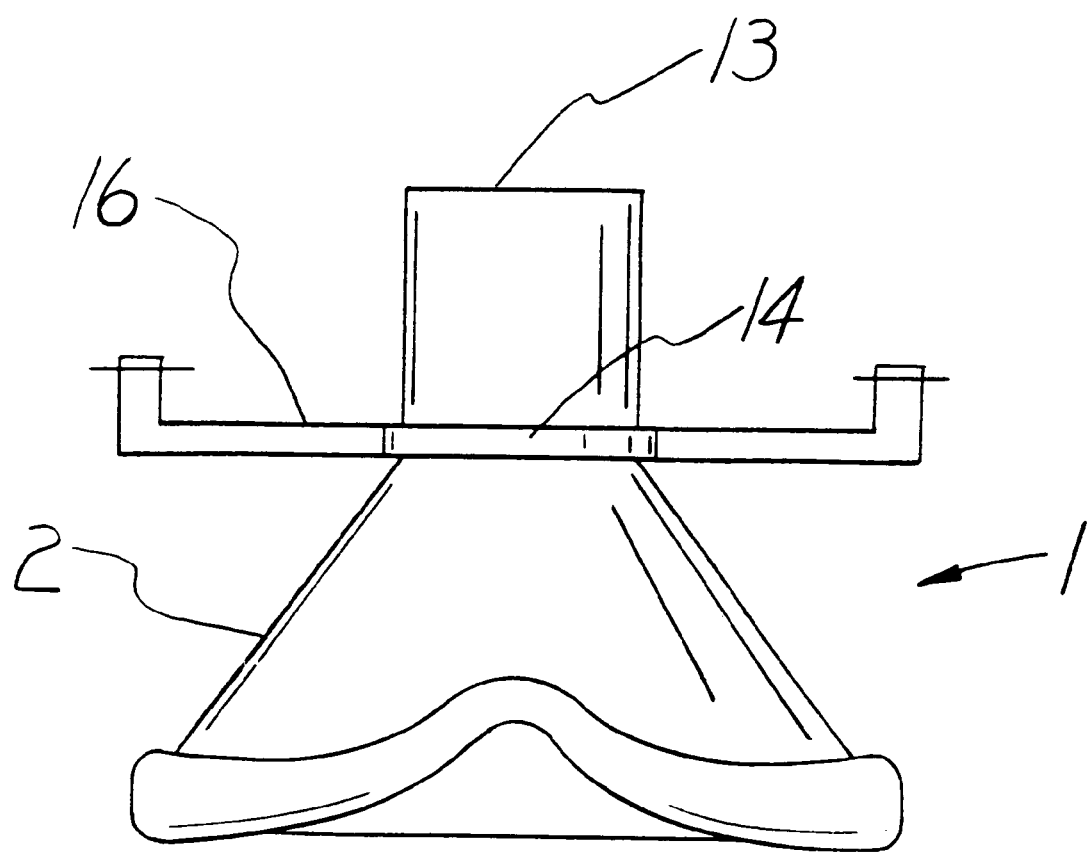
FIG. 1 is a bottom elevational view of a disposable anesthesia mask of the present invention.
Figure 2:
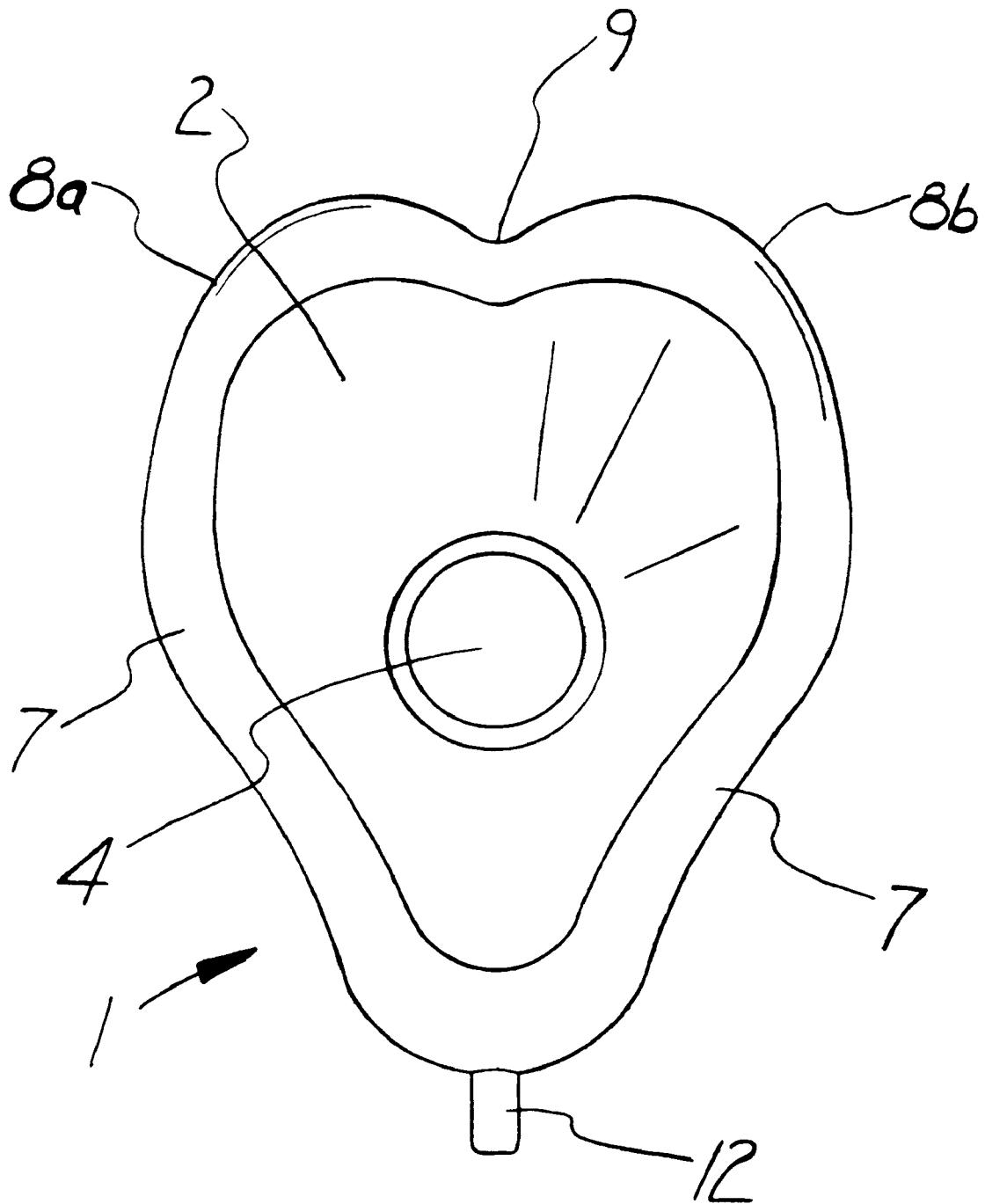
FIG. 2 is a front elevational view of a disposable anesthesia mask of the present invention.
Figure 3:
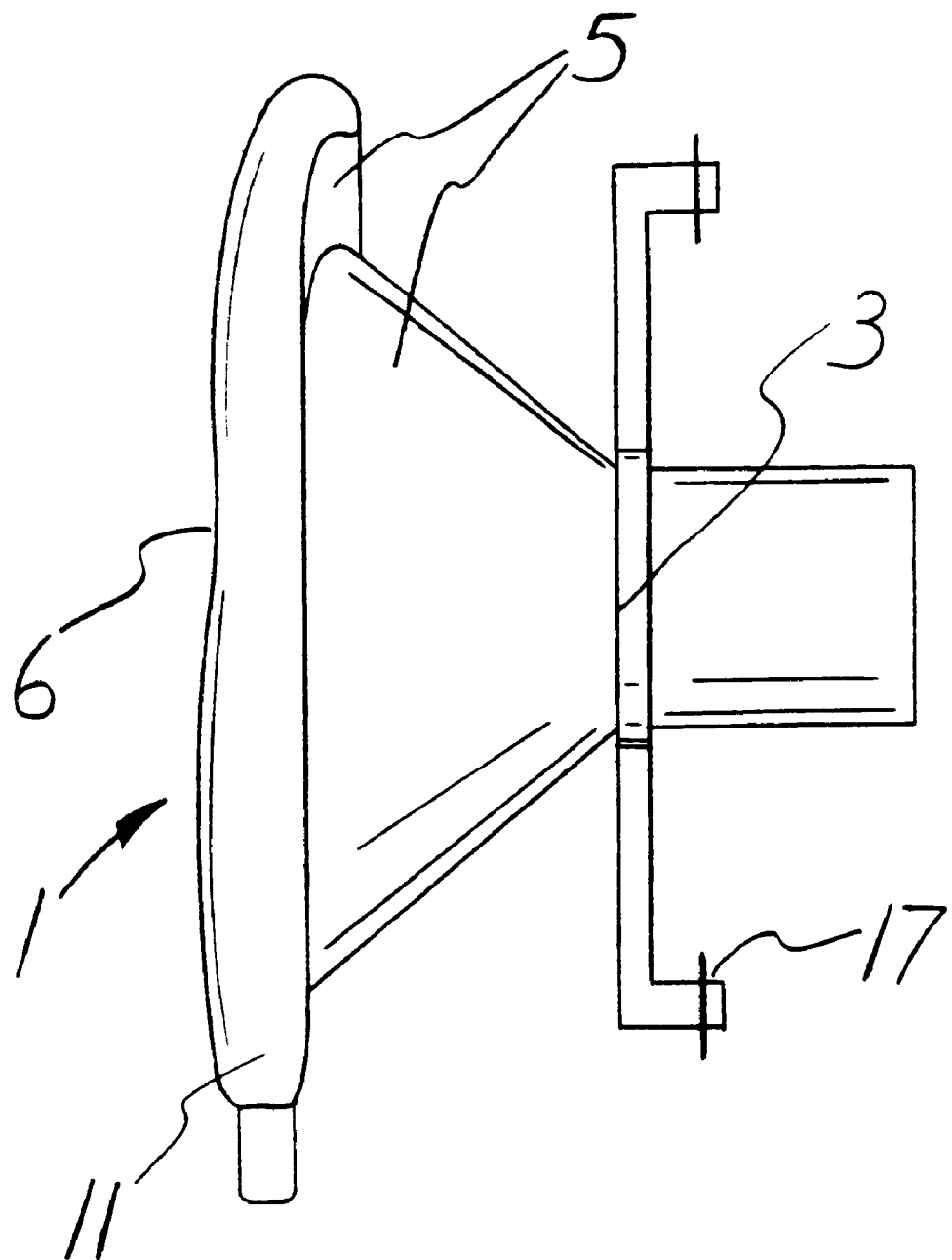
FIG. 3 is a side elevational view of a disposable anesthesia mask of the present invention.

FIGS. 1–3 represent various views of the disposable anesthesia mask 1 of the present invention. The mask 1 comprises a transparent polymeric resin body 2, which is concaved towards a patient's face (not illustrated). The concave or cup-shaped mask 1 has a top wall 3 having an aperture 4, an encompassing side wall 5, and an opened bottom 6 for receiving the nose and mouth of the patient.

The encompassing side wall 5 has a bottom portion 11, a top portion 9, and side portions 8a and 8b. The bottom portion 11 is in the shape of a horseshoe while the shape of the top portion 9 is of a serial double arch which has a constant radius of curvature for each arch. The side portions 8a and 8b bridge both ends of bottom portion 11 to their respective ends of top portion 9. The bottom portion further includes an edge which has a cardioid shape. This shape provides for the mask to curve around the nasal bridge and the oral tissues in order to confine the nasus and oris of a patient.

Affixed to the edge of the encompassing side wall is a soft pliable sealing material 7. The sealing material 7 is inflatable. A protruding nipple 12 is located at the bottom of the sealing material 7. An air pump (not illustrated) can be attached to this nipple 12 in order to enable for the inflation of the soft pliable material 11.

A portal 13 is located on the mask and is used for the induction of a variety of gases, such as oxygen, nitrogen and other anesthetic gases or the like. The portal 13 is a protruding hollow cylindrical tube which is attached to the aperture 4 of the top wall portion 3.

A head strap plate 14 is adapted to be removably fitted on the portal 13. Attached to and protruding outwardly from head strap plate 14 are a plurality of elongated rods 16. As illustrated in the figures, the rods are perpendicular to the portal. Each rod has a length of at least 1.5–2 inches. Located on the outer ends of each rod is a hook 17. These hooks receive and maintain a strap (illustrated and discussed in further detail in FIG. 4) that can be used in combination with the mask. The arrangement and design of the rods and hooks attached to the portal provides for the strap not to contact the patient when the mask is in utilization. Located at the outer ends of each hook 17 are ring shaped strap seats (illustrated in FIGS. 1 and 3 but not labeled). These strap seats maintain the strap in a fixed position. These strap seats provide a resting means for the strap and also provide a stop so that the strap does not travel downward on the hook.

Typically there would be four elongated rods that are affixed to the head strap plate. These rods are transverse from the axis of the portal and are 90 degrees from one another.

Figure 4:
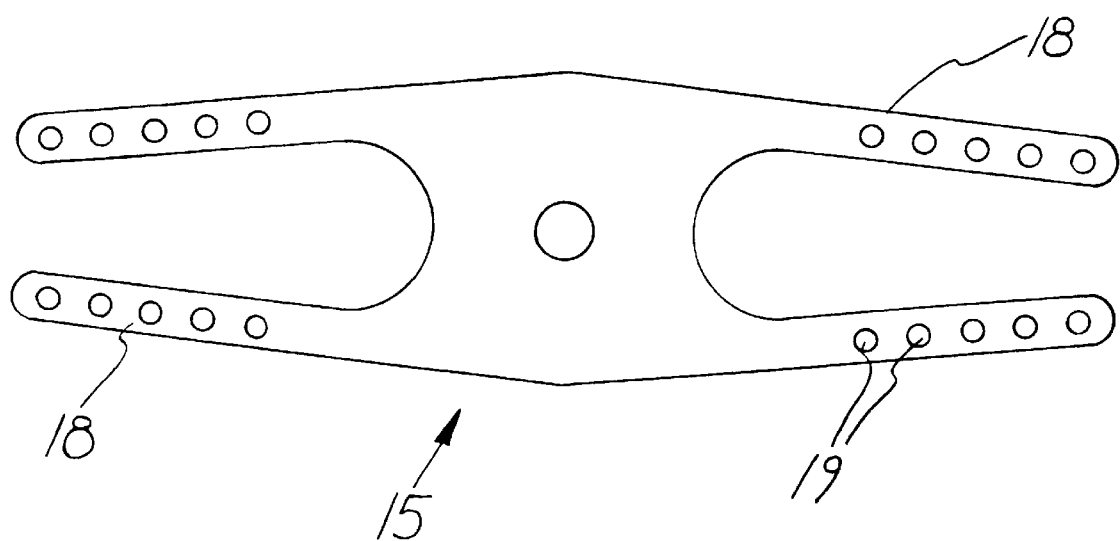
FIG. 4 is a perspective view of the strap of the present invention.

FIG. 4 illustrates a strap 15 which can be attached to the hooks on the mask. The strap 15 is a spider shaped design having a central body (not labeled) and a plurality of prongs 18. The number of prongs would correspond to the number of rods which are located on the head strap plate. The strap is made of a durable elastic material, such as rubber. Each prong 18 is equipped with several holes 19. The hooks on the strap receive the holes on the prong. This design provides for the holes to act as an adjusting means for the strap.

In order to utilize the mask of the present invention, it is first placed on the patient's face (not shown). Air is inducted through the nipple to inflate the sealing material. Once so inflated, the sealing material will provide a pneumatic seal around the patient's nasus and oris. An anesthesia gas inlet line and exhaust gas outlet line (neither shown) are attached to the portal to provide for a completed anesthetic circuit. Gases enter and exit the mask chamber through the portal and the aperture.

In order to attach the strap to the mask, the strap is first placed so that the central body is located against the back of the patients head. Then each of the prongs are wrapped around the patients head and are positioned so that a particular hole is aligned with a hook on the head strap plate. The choice of the particular hole will be dependent on the size of the patient's head. Each prong is then fitted onto the hook so that the hook protrudes through its selected hole. Each prong will come to rest on a ring seat, thereby providing a secure fit of the mask to the patient.

Due to the perpendicular placement of the rods with respect to the portal, the rods extended size of at least 1.5–2.0 inches, the hooks being perpendicular to the rods, and the placement of the seat ring at the hooks outer end, the prongs of the strap will not communicate with the patients face.

While the invention has been particularly shown and described with reference to an embodiment thereof, it will be understood by those skilled in the art, that various changes in form and detail may be made without departing from the spirit and scope of the invention.

We claim:

1. A disposable anesthesia mask to be used with a patient comprising:
    a cup-shaped base member;
        said cup-shaped base member made from a synthetic polymeric resin;
        said cup-shaped base member being transparent;
        said cup-shaped base member having an upper wall portion, an encompassing side wall, and an open bottom;
        said upper wall portion having an aperture;
        said open bottom having an edge portion;
            said edge portion having a cardioid shape for providing said edge portion with an upper portion comprising two arcuate members in series, and a lower portion comprising a single narrow arcuate member, said upper portion being wider than said lower portion;
    a pneumatic sealing means located on said edge portion;
        said pneumatic sealing means providing a pneumatic seal between said mask and said patient;
        said pneumatic sealing means encompassing a nasal bridge and a mouth area of a patient;
        said pneumatic sealing means being formed from a soft and pliable material which contours to a face of said patient;
    a portal;
        said portal being a protruding portion extending from said upper wall;
        said portal is located above said aperture;
        said protruding portion being a hollow tube;
        said protruding portion and said cup-shaped base are integral;
    a head strap plate;
        said head strap plate is adapted to be removably affixed to said protruding portion;
        said head strap plate includes a plurality of elongated rods;
        said plurality of elongated rods extend perpendicularly and outwardly from said protruding portion;
        each of said plurality of elongated rods having an outer end; and
    a hook extends outwardly and perpendicularly from each outer end of said plurality of elongated rods.

2. A disposable anesthesia mask as in claim 1 wherein a rap is adapted to be removably secured to said plurality hooks.

3. A disposable anesthesia mask as in claim 2 wherein said plurality of rods have a length of at least 1.5 inches.

4. A disposable anesthesia mask as in claim 2 wherein said strap includes a body portion;
    a plurality of prongs extend from said body portion;
        each of said plurality of prongs includes a plurality of holes; and
            said plurality of hooks receive said plurality of holes in said plurality of prongs.

5. A disposable anesthesia mask as in claim 2 wherein said other end includes a seating ring.

* * * * *